United States Patent [19]
Baile et al.

[11] 3,962,448
[45] June 8, 1976

[54] 8-ALKYL AND ALKENYL-10-HYDROXY-5H[1]BENZOPYRANOPYRIDINE DERIVATIVES HAVING POLYPHAGIC ACTIVITY

[75] Inventors: Clifton A. Baile, Glen Mills, Pa.; Paul E. Bender, Willingboro, N.J.; Bernard Loev, Broomall, Pa.

[73] Assignee: SmithKline Corporation, Philadelphia, Pa.

[22] Filed: Apr. 21, 1975

[21] Appl. No.: 570,130

Related U.S. Application Data

[62] Division of Ser. No. 450,118, March 11, 1974, Pat. No. 3,986,137.

[52] U.S. Cl. .............................................. 424/263
[51] Int. Cl.² ........................................ A61K 31/44
[58] Field of Search ................................... 424/263

Primary Examiner—Stanley J. Friedman
Attorney, Agent, or Firm—William H. Edgerton

[57] ABSTRACT

8-Alkyl and alkenyl-10-hydroxy-5H[1]benzopyranopyridines are prepared by dehydrogenation of the corresponding N-benzyl or N-hydrogen-8-alkyl or alkenyl-1,2,3,4-tetrahydro-5H[1]benzopyranopyridines in a high boiling solvent in the presence of a noble metal dehydrogenation catalyst. Alkyl derivatives of 5–11 carbon atoms are particularly useful. Also the O-acetyl derivatives are very useful. The compounds are central nervous system depressants and animal polyphagic agents.

9 Claims, No Drawings

8-ALKYL AND ALKENYL-10-HYDROXY-5H[1]BENZOPYRANOPYRIDINE DERIVATIVES HAVING POLYPHAGIC ACTIVITY

This is a division of application Ser. No. 450,118 filed Mar. 11, 1974, now U.S. Pat. No. 3,986,137, issued July 22, 1975.

This invention comprises new 8-alkyl-10-hydroxy-5H[1]benzopyrano[3,4]pyridine derivatives as well as methods and compositions using these benzopyranopyridines as active ingredients for inducing central nervous system depression, inhibiting gastric acid secretion or, especially, inducing polyphagia in meat producing animals such as pigs, sheep or cattle.

The structure of the compounds of this invention is characterized by the presence of a condensed [3,4-c or d]pyridine ring attached to the basic 10-hydroxy-8-alkyl-5H[1]benzopyran ring; for example,

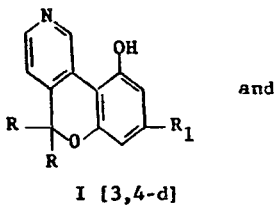 and 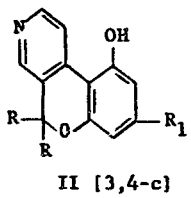

I [3,4-d]     II [3,4-c]

in which R is hydrogen or lower alkyl such as ethyl or preferably methyl and $R_1$ is straight or preferably branched alkyl of from 1–20, preferably 5–12 carbon atoms, such as methyl, ethyl, amyl, isoamyl, hexyl, 2-heptyl, n-nonyl, decyl, 1,2-dimethylheptyl, 1,1-dimethylheptyl, 1-ethylheptyl, 1,1,2-trimethyloctyl, 2-methylheptyl, 1-methylhexyl, 1,2-dimethyldecyl, 2-isoamyl and n-hexadecyl or alkenyl of 2–20, preferably 5–12 carbon atoms, such as 1,2-dimethylhepten-1-yl, allyl, vinyl, 2,6-dimethylocten-1-yl, undecen-10-yl or octadecen-9-yl. Preferably R is methyl and $R_1$ is 1,2-dimethylheptyl or 1,1-dimethylheptyl.

Included in this invention are the ether and ester derivatives of the compounds of Formulas I and II at the 10-hydroxy position. Most practically these derivatives will be of not more than 10 carbon atoms such as lower alkyl of 1–10, preferably 1–5 carbon atoms, such as methyl, ethyl or isopropyl, hydroxyethyl, dimethylaminoethyl or methoxyethyl or lower alkanoyl of 2–10, preferably 2–5 carbon atoms, such as acetyl, propionyl, dimethylaminopropionyl; carbamyl, dimethylcarbamyl, phosphoryl or other derivatives of similar phenolic hydroxyl groups as prepared and described in British Pat. No. 1,303,529, U.S. Pat. Nos. 3,514,464, 3,493,579, 3,635,993, French Pat. 2,068,516, U.S. Pat. No. 3,522,260, U.S. Pat. No. 3,576,798, U.S. Pat. No. 3,429,889 and U.S. Pat. No. 3,535,327.

The compounds of Formulas I and II may exist as optical isomers particularly due to the asymmetrical forms of certain branched chain alkyl substituents in the phenyl ring. These may be separated if desired by methods known to the art and are a part of this invention. Also included are the position isomers of the compounds of Formulas I and II in which the 10-hydroxy and 8-alkyl or alkenyl moieties are in other of the benz-positions of the benzopyran ring such as especially the 8-hydroxy-9-alkyl or alkenyl isomers. Starting materials for these compounds are prepared by methods using 4-alkyl-1,3-resorcinols in place of the 5-alkyl resorcinols of the Examples as described in *Tetrahedron* 23, 77 (1967).

Also salts of the bases of Formulas I and II are formed with nontoxic, pharmaceutically acceptable organic and preferably inorganic acids which normally form salts with pyridine for example the hydrochloride, hydrobromide, sulfate, citrate, sulfamate, toluenesulfonate, ethanedisulfonate, nitrate or phosphate salts. Quaternary salts with standard quaternizing agents are also part of this invention such as those with lower alkyl iodides, bromides or chlorides especially with methobromide, iodide or chloride and the ethobromide, iodide or chloride as well as the salt with toluenesulfonyl chloride. Salts of the phenolic hydroxyl group are also formed, especially those with alkali metals such as the potassium or sodium salt.

The salts in general are prepared by methods well known in the art most usually by reaction of the bases with the salt forming agent in ether, ethanol, ethyl acetate, etc., or a mixture such as aqueous ethanol, ether-water, etc. Other examples of similar salts and methods of forming these are disclosed in U.S. Pat. No. 3,576,798 and other references noted above.

The closest prior art compounds as far as applicants are aware are the corresponding compounds having a piperidine ring fused to the basic benzopyran nucleus. By this we mean that the structure is aliphatic at the [3,4-c and d] position since it is a tetrahydro derivative rather than an aromatic as with the compounds of this invention. Reference in the representative prior art may be had to Shulgin, U.S. Pat. No. 3,522,260; Pars et al., *J. Amer. Chem. Soc.* 88, 3664 (1966); and Dewey et al., *Nature* 226, 1265 (1970). The latter paper reports that the introduction of a nonaromatic N-heterocyclic moiety into the structure gave compounds not significantly different or quite less active than the naturally occuring compounds.

We have found, contrary to the teaching of the art in the aliphatic series, the compounds of our invention are extremely active CNS depressants and have some antisecretory activity in standard phamacological tests. For example 5,5-dimethyl-10-hydroxy-8-(3-methyl-2-octyl)-5H[1]benzopyrano[3,4-d]pyridine hydrochloride has significant anti-gastric acid secretion activity in pylorus ligated rats at 11 mg./kg. orally demonstrating a pH rise of +0.97 units. The same compound was inactive in the chronic gastric fistula test. This compound in rats dosed orally demonstrated at 0.5 mg./kg. slight hypothermia; at 1.0 mg./kg. moderate to marked decreased motor activity, low body posture and moderate ptosis; and at 2.5 mg./kg. marked decreased motor activity, low body posture, ptosis, catalepsy and marked hypothermia. 5,5-Dimethyl-8-(1,2-dimethylheptyl)-10-hydroxy-5H-benzopyrano[3,4-c]pyridine hydrochloride produced similar slight, moderate or marked CNS symptoms at 10, 25 and 50 mg./kg.

By contrast a representative tetrahydropyridine of the prior art (U.S. Pat. No. 3,535,327), namely 2-benzyl-5,5-dimethyl-10-hydroxy-8-(3-methyl-2-octyl)-1,2,3,4-tetrahydro-5H[1]benzopyrano[3,4-d]pyridine demonstrates slight to moderate CNS depression in rats at an oral dose of 10 mg./kg. which is about 10–20 times less than does the comparable compound of the present invention as described above. The prior art 2-methyl congener also shows slight to moderate CNS depression only at 100 mg./kg.

The compounds of this invention are therefore useful to produce CNS depressant or antisecretory activity in warm blooded animals as active ingredients uniformly combined with injectable or ingestible carriers in pharmaceutical compositions such as tablets, capsules, powders, solutions for parenteral injection and the like. These are prepared as conventional formulations using preferably an acid addition salt. The dosage amounts depend on the weight of the animal and the potency of the active ingredient but will generally be an amount sufficient to induce the desired CNS depression or antisecretory activity without side effects such as ataxia. Such doses may be chosen from the range of about 0.5–50 mg./kg. of body weight of the subject animal in need of treatment. For the much preferred series of Formula I for example 5,5-dimethyl-8-(1,2-dimethylheptyl)-10-hydroxy-5H[1]benzopyrano-[3,4-d]pyridin hydrochloride the effective quantity of active ingredient may be chosen from the range of about 0.5–10 mg./kg. The methods of inducing CNS depression or antisecretory activity comprise the internal administration of an active but nontoxic quantity of the active ingredient of Formulas II or preferably I by internal administration, i.e. by injection or preferably orally, to a subject animal in need of such treatment. The dosage units may be administered from 1–5 times daily.

We have also unexpectedly discovered that the compounds of Formula II and especially of Formula I are effective polyphagic agents in immature meat producing animals such as pigs, cattle or sheep and are especially useful in feed of healthy ruminant animals. The utility of these benzopyranopyridines in inducing forced feeding was demonstrated by methods discussed in Baile et al., *Phys. Rev.* 54, 160–214 (1974). Also this utility is discussed extensively in this publication.

(A) Tests with
5,5-dimethyl-10-hydroxy-9-(3-methyl-2-octyl)-
5H[1]benzopyrano[3,4-d]pyridine hydrochloride Groups of 8 sheep of approximately 30 kg. weight were fed ad libitum on 24 hour intakes and recorded during the week. Animals were given fresh feed and allowed to eat one hour before i.v. injection of the test dose in dimethylsulfoxide saline carrier. Feed was weighed at 0, 30 and 120 minutes after injection.

| Dose/Sheep | N** | 0–30 m. | 30–120 m. | 0–120 m. |
|---|---|---|---|---|
| carrier | 29 | 27±4.1 | 26±4.7 | 53±6.1 |
| .125 mg. | 8 | 39±12 | 12±5.6 | 51±14 |
| carrier | 29 | 48±7.5 | 10±2.5 | 58±7.3 |
| .25 mg. | 8 | 155±21 | 37±9.2 | 192±23 |
| carrier | 30 | 60±6.5 | 19±3.1 | 78±7.0 |
| .5 mg. | 8 | 93±17 | 74±20 | 167±31 |
| 1 mg.* | 8 | 10±5.4 | 21±17 | 31±22 |

*CNS depression was noted at 1 mg.
**Number of animals.

Significant polyphagia was therefore demonstrated within the range of 5 to 20 µg./kg. of body weight, especially 0.25–0.5 µg./kg. Alternatively, polyphagia is observed within the range of 0.25–0.5 mg./sheep.

Twenty-four hour intakes of a meal type feed were measured routinely in 24 sheep. Eight sheep, which had intakes varying not more than 10% from the highest intake in 3 days, were offered the same diet with test chemical added uniformly in the feed carrier for 2 days. Two-day average intakes before, during and after the medicated feed were measured and were compared with paired-t test to determine the effect of the medicated feed on intakes.

| Dose(mg./kg.) | Pre-Test | Drug Effect | Post-Test |
|---|---|---|---|
| .05 | 1243±50 | 1211±39 | 1281±48 |
| .25 | 1436±69 | 1446±96 | 1447±83 |
| 1.0 | 1381±62 | 1501±71 | 1455±64 |
| 2.0 | 1382±99 | 1448±86 | 1354±81 |

Significant polyphagia was demonstrated orally with the active ingredient mixed feed at 1 mg./kg. of feed.

(B)
5,5-Dimethyl-8-(1,2-dimethylheptyl)-10-hydroxy-
5H[1]benzopyrano[3,4-c]pyridine hydrochloride

| Dose/Sheep | N* | 0–30 m. | 30–120 m. | 0–120 m. |
|---|---|---|---|---|
| carrier | 29 | 47±9.8 | 24±6.9 | 71±11 |
| 1 mg. | 8 | 55±10 | 67±28 | 122±30 |
| carrier | 29 | 47±7.1 | 27±4.9 | 75±9.0 |
| 2 mg. | 6 | 66±13 | 19±1.7 | 85±13 |
| .5 mg. | 7 | 46±17 | 42±9.8 | 89±21 |
| carrier | 29 | 62±10 | 33±5.3 | 95±11 |
| 4 mg. | 8 | 42±13 | 74±18 | 115±22 |

*Number of animals.

Therefore another aspect of this invention is veterinary compositions and methods for inducing polyphagia or forced feeding in immature meat producing animals comprising internal administration, preferably oral, of a quantity sufficient to induce polyphagia but not to exhibit toxic side effects such as severe CNS depression of a compound of Formula II or preferably Formula I or its equivalent. The subjects are pigs, sheep or cattle, preferably healthy ruminants. The quantity is chosen from the range of about 2.5–250 µg./kg. of body weight, preferably 5–20 µg./kg. depending on the potency and toxicity of the compound and the route of administration.

As a specific illustration of this invention, 5,5-dimethyl-10-hydroxy-8-(3-methyl-2-octyl)-5H[1]benzopyrano[3,4-d]pyridine hydrochloride in the range of about 0.75–1.25 mg./kg. of feed is mixed with a standard feed lot ration and fed ad libitum to healthy immature sheep or cows in a feed lot preliminary to shipping to market.

For commercial use, the active ingredients when used in the feed can be readily used as premix formulations in which the chemical is distributed uniformly throughout a standard animal feed carrier. This premix or concentrate is then mixed with a normal diet for the animal desired. Examples of such carriers are soybean meal, corn oil, ground corn, barley, wheat, corn gluten meal, corn distillers solubles, soyflour mineral mixtures such as vermiculite and diatomaceous earth. The active ingredient will be in amounts to satisfy the criteria set forth above for whole feed. The active ingredient will usually be present in from about 1–75% by weight of the premix composition.

The animal feeds themselves may also contain: roughages such as cellulose, hay, straw, silages, corn stalks, cotton seed hulls, oats, barley and cereal brans; natural oils such as animal fats, fish oils, safflower oil, peanut oil, and cottonseed oil; antioxidants, minerals, vitamins, antibiotics, anthelmintics; and other appropriate medicaments.

Examples of typical prepared animal feed is as follows:

| Ingredients | Weight per cent | |
|---|---|---|
| Mixed hay | 40.0 | |
| Ground yellow corn | 45.0 | |
| Soybean oil meal | 7.0 | |
| Cane molasses | 7.0 | |
| Dicalcium phosphate | 0.5 | |
| Trace minerals salt | .5 | |
| Vitamin A | 300 | I.U./lb. |
| Vitamin D | 150 | I.U./lb. |
| Active ingredient | 1 | mg./kilo of feed |

The use by intramuscular injection or by implant may also be used by methods well known to the art. The active ingredients of Formulas I and II are mixed uniformly with an injectable carrier, then administered to healthy growing animals from 1–3 times during the growing or fattening period. Methods of preparing and using implant compositions are described in U.S. Pat. No. 3,428,729, *J. Animal Science* 27, 1772 (1968) or *J. Biomed. Mater. Res.* 1, 433 (1967).

The new compounds of this invention are prepared by dehydrogenation of the corresponding N-benzyl-1,2,3,4-tetrahydropyridine derivative. Alternatively the N-hydrogen-1,2,3,4-tetrahydropyridine derivatives may be dehydrogenated under reaction conditions mentioned hereafter. The starting materials are known to the art; see, for example, Example 2 of U.S. Pat. No. 3,514,646 or Example 1 of U.S. Pat. No. 3,535,327. They are prepared starting with the reaction of a known 5-alkyl resorcinol with either N-benzyl-3-carbethoxy-4-piperidone for the preferred [3,4-d]pyridines of Formula I or N-benzyl-4-carbethoxy-3-piperidone for the preferred [3,4-d]pyridines of Formula I. Other alkyl derivatives are made by substituting the known 5-alkylresorcinol. Other 5,5-dialkyl groups are prepared by using the appropriate Grignard reagent during the synthetic procedures in the prior art patents.

The 3-benzyl-5,5-dilower alkyl-8-alkyl-1,2,3,4-tetrahydro-5H[1]benzopyrano[3,4-d]pyridine derivative is heated, usually at reflux, in a high boiling solvent in which it is at least partially soluble such as p-cymene, xylene, durene, isodurene and the like in the presence of a noble metal dehydrogenation catalyst such as Pd/C, Pt/C, Raney nickel or, in the debenzyl series, sulfur, dichloroquinone or other dehydrogenation reagents. The reaction most usually proceeds at from 30 minutes to several hours. It will be appreciated that, using the noble metal catalyst method such as Pd/C or Pt/C, debenzylation and dehydrogenation unexpectedly occurs in one step.

The product is isolated from the cooled mother liquor after filtration as the base by evaporation in vacuo or by reaction with an ethereal acid to form an appropriately insoluble acid addition salt.

Alternatively to the N- or 3-benzyl moiety other hydrogenation labile groups known to the art may be used in the dual reaction step of this invention such as trivially substituted benzyl, benzhydryl or trivially substituted benzhydryl moieties. No particular advantage is apparent in these other moieties however and, therefore, the N-benzyl derivative of the tetrahydro starting material is most often used.

Ethers of the 10-hydroxy group are prepared as known to the art most usually by common reactions such as alkyl or substituted alkyl halide in an inert organic solvent in the presence of an acid acceptor. Sodium carbonate-ethanol, sodium hydride-glyme or potassium hydroxide-dimethylformamide are often used. The latter two are preferred. Ester derivatives of the 10-hydroxy group are prepared by reacting the appropriate acid chloride, mixed ester or an anhydride in an inert solvent plus an acid acceptor. Often a tertiary amine solvent is used such as pyridine or dimethylaniline. The esters may also be prepared by reaction of the appropriate acid with a dehydrating agent such as dicyclohexylcarbodiimide. See the references noted above for more details or Examples 24, 25, 26, 27, 28 or 29 or U.S. Pat. No. 3,514,464.

As used hereabove the terms "lower alkyl" or "lower acyl" are defined as including those individual terms usually known or used in the art such as phenolic derivatives at position 10 of Formulas I and II but for practical purposes are limited to up to 10 preferably up to 5 carbon atoms. No particular advantage is apparent in the larger groups so methyl or ethyl esters, acetyl or phosphoryl esters are most useful. The O-acetyl derivatives are very active, stable and are especially preferred among the O-derivatives.

The following examples are intended to teach the chemical preparation of the compounds of this invention but are not intended to limit the scope of the claims.

EXAMPLE 1 a. A slurry of 2-benzyl-5,5-dimethyl-10-hydroxy-8-(1,2-dimethylheptyl)-1,2,3,4-tetrahydro-5H[1]benzopyrano-[3,4-d]pyridine (1.4 g., 3.2 mmol., U.S. Pat. No. 3,535,327) in 25 ml. of dried cymene is added over 20 minutes to a stirred, refluxing suspension of palladium-on-charcoal (360 mg.) in 50 ml. of dried cymene under a stream of nitrogen. After 1 hour at reflux, the suspension is cooled then filtered. An excess of ethereal hydrogen chloride is added to the filtrate to separate the solid hydrochloride salt of 5,5-dimethyl-8-(1,2-dimethylheptyl)-10-hydroxy-5H[1]benzopyrano[3,4-d]pyridine, m.p. 252°–254°C. 79% Yield after recrystallization from ethanol.

b. The base from (a) is obtained by shaking 25 mg. of the hydrochloride in sodium bicarbonate-ether. The dried ether mixture is divided into aliquots and reacted with acetic anhydride in pyridine to give the 10-acetoxy; methyl iodide in the presence of sodium methoxide to give the 10-methoxyl; with sulfamic acid to give the sulfamate salt; with ethyl iodide in ether to give the quaternary salt; with sulfuric acid in ether to give the sulfate salt; and with potassium hydroxide in aqueous ethanol to give the potassium salt.

EXAMPLE 2

Using similar amounts and the same procedure as in Example 1 but with 3-benzyl-5,5-dimethyl-10-hydroxy-8-(1,2-dimethylheptyl)-1,2,3,4-tetrahydro-5H[1]benzopyrano-[3,4-c]pyridine gives a 76% yield of 5,5-dimethyl-8-(1,2-dimethylheptyl)-10-hydroxy-5H[1]benzopyrano[3,4-c]pyridine hydrochloride, m.p. 259°–263°C.

EXAMPLE 3

Reaction of 2-benzyl-10-hydroxy-5,5,8-trimethyl-1,2,3,4-tetrahydro-5H[1]benzopyrano[3,4-d]pyridine (100 mg., U.S. Pat. No. 3,535,327) with Pd/C in boiling cymene gives 10-hydroxy-5,5,8-trimethyl-5H[1]benzopyrano[3,4-d]pyridine.

EXAMPLE 4

Reacting 3-benzyl-5,5-diethyl-10-hydroxy-8-methyl-1,2,3,4-tetrahydro-5H[1]benzopyrano[3,4-c]pyridine, (200 mg., prepared by substituting ethyl magnesium iodide in Example 8 of U.S. Pat. No. 3,514,464) with Pd/C in refluxing cymene for 2 hours gives 5,5-diethyl-10-hydroxy-8-methyl-5H[1]benzopyrano[3,4-c]pyridine as the hydrobromide.

EXAMPLE 5

Substituting known 5-(2-tetradecyl)resorcinol, 5-(3-cyclopropyl-2-propyl)resorcinol, 5-(1-cyclohexylethyl)-resorcinol, 5-(2-eicosyl)resorcinol, 5-(1,1-dimethylheptyl)-resorcinol, 5-(2-heptyl)resorcinol, 5-(n-amyl)resorcinol, 5-(2-methylheptyl)resorcinol, 5-(1-ethylheptyl)resorcinol, 5-(1,2-dimethylhexyl)resorcinol or 5-(1-methylene-2-methylheptyl)resorcinol (*J. Med. Chem.* 16, 1205 (1973) which also describes other methods of making 5-alkyl and 5-alkenyl resorcinols) in Example 1 of U.S. Pat. No. 3,535,327 and Example 1 above gives the corresponding 8-alkyl or 8-alkenyl-5,5-diethyl-10-hydroxy-5H[1]benzopyrano[3,4-d]-pryidines and salts.

EXAMPLE 6

A solution of 6 g. of 2-benzyl-10-hydroxy-8-(3-methyl-2-octyl)-5-oxo-1,2,3,4-tetrahydro-5H[1]benzopyrano-[3,4-d]pyridine (U.S. Pat. No. 3,535,327) in 50 ml. of dry tetrahydrofuran is added with cooling to a stirred suspension of 2.4 g. of lithium aluminum hydride in tetrahydrofuran over a period of 45 minutes. After refluxing for 2 hours, the reaction mixture is cooled, treated with ethyl acetate and sodium sulfate. The filtrate therefrom is dried and concentrated in vacuo to give a triol. This is dissolved in 200 ml. of dioxane-water (1:1), 10 ml. of dil.hydrochloric acid is added and refluxed 3 hours. The solvents are then removed and the residue is dried and distilled to give 2-benzyl-10-hydroxy-8-(3-methyl-2-octyl)1,2,3,4-tetrahydro-5H[1]benzopyrano[3,4-d]pyridine. This compound (1 g.) is heated at reflux with Pd/C in cymene in the method of Example 1(a) to give 10-hydroxy- 8-(3-methyl-2-octyl)-5H[1]benzopyrano[3,4-d]pyridine which on dissolving in ethereal hydrochloric acid gives the hydrochloride.

What is claimed is:

1. A veterinary composition having polyphagic activity comprising as an active ingredient dispersed in an injectable or ingestible carrier a polyphagic but nontoxic quantity selected from the range of about 2.5–250 $\mu$/kg. of body weight of a compound or a nontoxic, pharmaceutically acceptable salt thereof, said compound having the structure:

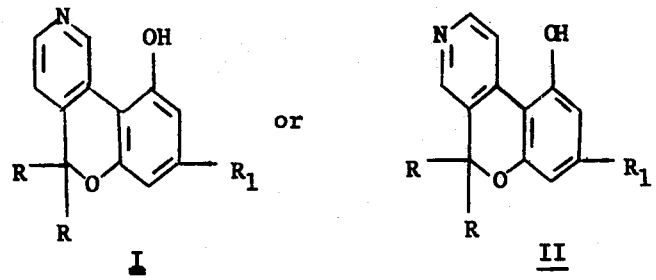

in which R is hydrogen, methyl or ethyl and $R_1$ is a straight or branched alkyl of from 1–20 carbon atoms.

2. The composition of claim 1 in which the pyridino ring is in the 3,4-d configuration.

3. The composition of claim 2 in which $R_1$ is 1,2-dimethylheptyl in the form of the base or an acid addition salt thereof.

4. The composition of claim 2 in which $R_1$ is 1,1-dimethylheptyl in the form of the base or an acid addition salt thereof.

5. The method of inducing polyphagic acitivity in healthy, immature ruminant animals comprising administering by injection or orally to said animals a polyphagically effective but nontoxic or nondepressant quantity of an active ingredient having the structure:

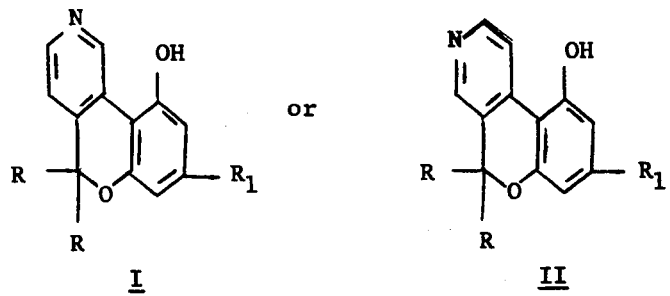

in which R and $R_1$ are as defined above in claim 1.

6. The method of claim 5 in which the administration is oral and the compound is 5,5-dimethyl-8-(1,2-dimethylheptyl)-10-hydroxy-5H[1]benzopyrano[3,4-d]pyridine or an acid addition salt thereof.

7. The method of claim 5 in which the administration is oral and the compound is 5,5-dimethyl-8-(1,1-dimethylheptyl)-10-hydroxy-5H[1]benzopyrano[3,4-d]pyridine or an acid addition salt thereof.

8. The method of claim 5 in which the quantity of active ingredient is selected from the range of 2.5–250 $\mu$/kg. of body weight.

9. The method of claim 5 in which the administration is orally in a quantity selected from the range of from about 0.75–1.25 mg./kg. of feed ration and the active ingredient has a structure in which $R_1$ is an alkyl of from 5–11 carbons and the pyridine ring is in the 3,4-d configuration.

* * * * *